United States Patent [19]
Alkaeva et al.

[11] Patent Number: 5,728,837
[45] Date of Patent: Mar. 17, 1998

[54] METHOD OF OBTAINING NICOTINIC ACID

[75] Inventors: Evgenia Moiseevna Alkaeva; Tamara Vitalievna Andrushkevich; Galina Alexeevna Zenkovets, all of Novosibirsk; Mikhail Grigorievich Makarenko, poselok Krasnoobsk, all of Russian Federation

[73] Assignee: Institut Kataliza Imeni G.K. Boreskova Sibirskogo Otdelenia Rossiiskoi Akademii Nauk, Russian Federation

[21] Appl. No.: 676,352

[22] PCT Filed: Jan. 26, 1995

[86] PCT No.: PCT/RU95/00013

§ 371 Date: Jul. 17, 1996

§ 102(e) Date: Jul. 17, 1996

[87] PCT Pub. No.: WO95/20577

PCT Pub. Date: Aug. 3, 1995

[30] Foreign Application Priority Data

Jan. 26, 1994 [RU] Russian Federation ............ 94003019

[51] Int. Cl.$^6$ .............. C07D 213/127; C07D 213/80; C07D 213/79; C07D 213/803
[52] U.S. Cl. ............ 546/320; 546/327; 546/319
[58] Field of Search ..................... 546/320, 327

[56] References Cited

U.S. PATENT DOCUMENTS

| 2,586,555 | 2/1952 | Mueller ................. 546/320 |
| 4,001,257 | 1/1977 | Masuda et al. ........... 546/320 |

FOREIGN PATENT DOCUMENTS

| 1940320 | 8/1972 | Germany . |
| 532578 | 2/1973 | Switzerland . |
| 543510 | 12/1973 | Switzerland . |
| 235764 | 1/1969 | U.S.S.R. . |
| 1368309 | 9/1974 | United Kingdom . |

OTHER PUBLICATIONS

Rubtsov, M.V., et al. "Preparation of Nicotonic ..." *Short Notices* pp. 315–317. (in Russian w/English translation) 1957.

Järas, Sven, et al. "Preparation of Pyridinemonocarboxylic ..." *J. Appl. Chem. Biotechnol.* 1977, 27, pp. 499–509.

*Primary Examiner*—Alan L. Rotman
*Attorney, Agent, or Firm*—Ladas & Parry

[57] ABSTRACT

A method has been developed for preparing nicotinic acid with a yield of 82–86% mol. in which method there is no formation of harmful gas wastes and liquid wastes.

The process is carried out by gas-phase single-step oxidation of β-picoline with oxygen in the presence of water vapor and a catalyst on the base of oxides of vanadium and titanium, with or without additives, at a temperature of 250°–290° C. and mole ratios $O_2$:β-picoline=15–40 and $H_2O$:β-picoline= 10–70.

7 Claims, No Drawings

METHOD OF OBTAINING NICOTINIC ACID

CROSS-REFERENCE

This application is a 371 of PCT/RU95/00013 filed Jan. 26, 1995.

FIELD OF THE INVENTION

The invention relates to a process for preparing nicotinic acid. Nicotinic acid and its derivatives have a wide variety of physiological properties, due to which they are widely used in medicine and agriculture as vitamins, drugs, and growth regulators for plants.

BACKGROUND OF THE INVENTION

Several processes for synthesis of nicotinic acid are known: 1) By liquidphase oxidation of β-picoline using as the oxidant $KMnO_4$ (M. R. Rubtsov, L. N. Yakhontov, S. V. Yatsenko, ZhPKh, 1957, v. 30, No. 2, pp. 315–318), and also $HNO_3$ and $H_2SO_4$ (U.S. Pat. No. 2,586,555, 1952); 2) By oxidative ammonolysis of β-picoline in the presence of a vanadium catalyst with subsequent hydrolysis of nicotinonitrile into nicotinic acid (USSR Inventor's Certificate No, 235764, published B.I. No. 6, 1969).

Liquid phase oxidation of β-picoline using the oxidants indicated above takes place at a high selectivity at a temperature of 75°–300° C. The yield of nicotinic acid in such processes is 66–77%. Substantial drawbacks of these processes include their periodicity, multistage execution, complexity of technological execution, low productivity, large amount of waste water and solid wastes containing harmful substances.

The preparation of nicotinic acid through oxidative ammonolysis of β-picoline is carried out at a temperature of 350°–400° C. with a high productivity and a high yield (86–88%), but includes many steps, in particular,
1) catalytic synthesis of nicotinonitrile;
2) extraction of nicotinonitrile with petroleum ester from a mixture of liquid products of the reaction;
3) rectification of the ester stretching;
4) hydrolysis of the nicotinonitrile;
5) recrystallization of nicotinic acid from ethyl alcohol.

The process is also characterized by a large number of harmful liquid wastes and waste gases comprising ammonia.

One more process for preparing nicotinic acid is known (Sven Jaras, Sten T. Lundin. Preparation of pyridinemonocarboxylic acids by catalytic vapor phase oxidation of alkylpyridineI.—J.Appl. Chem. Biotechnol., 1977, 27 pp.499–509). According to this process nicotinic acid is prepared by direct single step gas-phase oxidation of β-picoline with oxygen in the presence of nitrogen and an aqueous vapor on an oxide catalyst located in a tubular reactor. Wherein the reaction temperature is 350°–460° C., space velocity of the gaseous mixture is 1450–2600 $h^{-1}$ (contact time is 2.5–1.4 s), mole ratios $O_2$:β-picoline=42, $H_2O$: β-picoline=82. The catalyst is prepared by melting a mixture of $V_2O_5$ and $TiO_2$ at a temperature of 1250° C. in the course of 3 hours. The specific surface of the catalyst thus prepared is 0.2–1.0 $m^2$/g. Granules having a size of 0.5–1.5 mm are loaded into a reactor. When the process is carried out under these conditions the maximum yield of nicotinic acid is 48%. Products of the reaction are, in addition to nicotinic acid, β-pyridine carbaldehyde, pyridine, CO, $CO_2$ and HCN. Harmful waste gases comprising CO and HCN are formed in the reaction process. The nicotinic acid is gathered in a condensate comprising, furthermore, unreacted β-picoline, 3-pyridine carbaldehyde, pyridine and resin-like products. The isolation of nicotinic acid from the condensate is carried out using a complex multistage process including extraction of β-picoline and β-pyridine carbaldehyde with chloroform from an aqueous solution with the subsequent isolation of nicotinic acid from the aqueous phase. Wherein liquid harmful wastes are formed which need to be recovered, and the nicotinic acid may be contaminated by chloroform ingredients which makes purification more difficult.

The data provided above show that the described process has the following drawbacks:
1) Harmful gas wastes and resins, contaminating the nicotinic acid and making its isolation and purification more difficult, are formed in the process of preparing nicotinic acid;
2) A low yield of nicotinic acid, which does not exceed 48%.

Therefore, the existing processes of preparing nicotinic acid are characterized by a large number of harmful liquid wastes and gas wastes, by the formation of resin-like products, and with single-step oxidation of β-picoline by the low yield of nicotinic acid.

Disclosure of the Invention

The object of the present invention is to create such a process for preparing nicotinic acid which would make it possible to increase the yield of the desired product and exclude the formation of harmful waste gases and resins.

This object is achieved by proposing a process for preparing nicotinic acid by gas-phase single-step oxidation of β-picoline with oxygen in the presence of nitrogen and aqueous vapor on an oxidative catalyst. In this process, in accordance with the invention, the process of oxidation is carried out in a tubular reactor on a catalyst having a composition $nV_2O_5mTiO_2.pM_xO_y$ (where M is an alkaline metal or a transition element, n=5–75% by weight, m=95–25% by weight, p=0–1% by weight) at a temperature of 250°–290° C., space velocity of the gas mixture 2400–13300$h^{-1}$ (contact time—1.5–0.27 s), mole ratios $O_2$:β-picoline=15–40, $H_2O$: β-picoline=10–70. Isolation of pure nicotinic acid (99.5%) is effected right after the reactor in a tube-crystallizer at a temperature of 160°–200° C.

Only the maintenance of an optimum temperature range for carrying out the reaction (250°–290° C.) results in the achievement of the object of the invention: to increase the yield of the desired product and exclude the formation of harmful gas wastes and resin. If the temperature of the reaction is reduced to a value lower than 250° C. the activity of the catalyst drops and the danger of crystallization of the nicotinic acid directly in the reactor appears. If the temperature is increased to a value above 290° C. the yield of nicotinic acid is reduced, wherein the amount of products of deep oxidation is increased, and undesirable resin-like products appear. It is just using catalyst having a composition $nV_2O_5.mTiO_2.pM_xO_y$ with a specific surface of 10–120 $m^2$ that the object of the invention is achieved. When the content of $V_2O_5$ is reduced to below 5% by weight, the yield of nicotinic acid is reduced, and when that content is increased above 75% the yield of the acid is also reduced. When additives of alkaline metals or transition elements are introduced, the activity of the catalyst is increased, and a high yield of nicotinic acid is maintained.

The effectiveness of carrying out the reaction is ensured by optimum ratios of the concentrations of the components fed into the reactor. When the mole ratio $O_2$:β-picoline is reduced to less than 15, the activity of the catalyst drops, and when the ratio is increased to more khan 40, the selectivity in respect of nicotinic acid is reduced. When the mole ratio $H_2O$:β-picoline fills to less than 10, the activity of the catalyst is reduced, and when it is increased to above 70 the process can only be carried out at small concentrations of β-picoline, which results in a reduction of the productivity of the process.

Best Method of Carrying Out the Invention

The process for preparing nicotinic acid is simple in technological execution and is carried out in the following manner.

A gaseous mixture comprising β-picoline, oxygen, nitrogen and aqueous vapor, is passed through a catalyst in a flow-circulation plant and use is made of a differential reactor having a diameter of 18 mm. Wherein the temperature of the reaction is 250°–290° C., the space velocity of the gas mixture is 2400–13300 $h^{-1}$ (contact time is 1.50–0.27 s), the mole ratios $O_2$:β-picoline=15–40, $H_2O$:β-picoline= 10–70. The composition of the reaction mixture is analyzed chromatographically. The catalyst is prepared by mixing $TiO_2$ and an aqueous solution of vanadyl oxalate with subsequent thermal treatment. The additives are introduced from water-soluble salts. The specific surface of the thus prepared catalyst is 10–120 $m^2/g$. The catalyst in the form of 0.5–1.0 mm granules is loaded into the reactor. When the process is carried out under these conditions the maximum yield of nicotinic acid is 86%, calculations of a maximum yield in conditions of ideal displacement were made by kinetic equations, first order.

In addition to nicotinic acid, 3-pyridine carbaldehyde and $CO_2$ are products of the reaction. The waste gases comprise $CO_2$, $O_2$ and $N_2$, which are not harmful. Unreacted β-picoline, β-pyridine carbaldehyde and water are contained in the condensate and may be directed into the reactor for further conversion without additional separation. Nicotinic acid, uncontaminated by resins, is isolated from the gas-vapor mixture right after the reactor in a tubular crystallizer, where a temperature of 160°–200° C. is maintained. Its chemical composition (% by weight) is: nicotinic acid— 99.5, β-pyridine carbaldehyde—0.5. After purification by the simple method of recrystallization from water its external appearance and composition conform with pharmaceutical requirements. The melting point is 235.8°–237.3° C.

The proposed process for preparing nicotinic acid as compared with prior art is distinquished by its simplicity, by the absence of harmful effluents and resins and ensures an increased yield of the desired product (86%), which is greater than the index of the known process (48%) obtained under similar conditions (Sven Jaras, Sten T. Lundin. Preparation of pyridinemonocarboxylic acids by catalytic vapor phase oxidation of alkylpyridine. —J.Appl. Chem. Biotechnol., 1977, 27, pp. 499–509). Wherein the isolation of pure nicotinic acid is simplified. The composition of the condensate makes it possible to use it without additional separation for feeding into a reactor for reconversion into nicotinic acid.

The following concrete examples are presented for better understanding of the present invention.

EXAMPLE 1

Into a reactor were loaded 1.5 g of a vanadium-titanium oxidative catalyst comprising 5% by weight $V_2O_5$ and 95% by weight $TiO_2$, and at a temperature of 250° C. gaseous mixture of the following composition (% by volume) was inputted: β-picoline—0.4, O2—16, $H_2O$—28, $N_2$—balance. The contact time was 0.27 s. Nicotinic acid was isolated in a tube after the reactor at a temperature of 170° C. Its chemical composition (% by weight) was: nicotinic acid— 99.5, β-pyridincarbaldehyde—0.5. The degree of conversion of β-picoline in this example was 83.7%, the selectivity in respect of nicotinic acid—86.3%, in respect of β-pyridine carbaldehyde—4%, in respect of $CO_2$—9.7%. The calculated maximum yield of nicotinic acid in the ideal displacement mode was 83%.

EXAMPLES 2–9, 17, 18.

The nicotinic acid was prepared as in Example 1, except that as well as the contact time, the chemical composition of the catalyst was varied. The characteristics of the catalyst, conditions and results of the tests are presented in the Table.

EXAMPLES 10–11.

The nicotinic acid was prepared as in Example 5, except that as well as the contact time, the temperature of the reaction was varied. The characteristics of the catalyst, temperature of the reaction, other conditions and results of the tests are presented in the Table.

EXAMPLES 12–14

The nicotinic acid was prepared as in Example 5, except that as well as the contact time, the concentration ratio $O_2$:β-picoline was varied. The conditions and results of the tests are presented in the Table.

EXAMPLES 15–16

The nicotinic acid was prepared as in Example 5, except that as well as the contact time, the concentration ratio $H_2O$:β-picoline was varied. The conditions and results of the tests are presented in the Table.

Industrial Applicability

The proposed process for preparing nicotinic acid can be used in the chemical industry.

TABLE

| No ex. 1 | Composition of catalyst % by weight 2 | Catalyst surface m²/g 3 | t, °C. 4 | β-pic. concen. % by vol. 5 | Concentration ratio O₂: β-pic. 6 | H₂O: β-pic. 7 | Ideal displacement mode τ s 8 | X, % 9 | S, % nic. acid 10 | β-pyr-ald. 11 | CO₂ 12 | Re-sin 13 | Y, % 14 | IDM D, % 15 |
|---|---|---|---|---|---|---|---|---|---|---|---|---|---|---|
| 1 | 5V₂O₅—95TiO₂ | 120 | 250 | 0.4 | 40 | 70 | 0.27 | 83.7 | 86.0 | 4.0 | 9.7 | — | 72.0 | 83.0 |
| 2 | 10V₂O₅—90TiO₂ | 47 | 250 | 0.4 | 40 | 70 | 0.35 | 85.5 | 91.0 | 4.6 | 3.8 | — | 77.8 | 86.0 |
| 3 | 15V₂O₅—85TiO₂ | 27 | 250 | 0.4 | 40 | 70 | 0.61 | 86.6 | 93.0 | 3.5 | 3.5 | — | 80.5 | 86.0 |
| 4 | 17V₂O₅—83TiO₂ | 29 | 250 | 0.4 | 40 | 70 | 0.61 | 88.4 | 91.0 | 5.0 | 4.0 | — | 80.4 | 86.0 |
| 5 | 20V₂O₅—80TiO₂ | 29 | 250 | 0.4 | 40 | 70 | 0.75 | 86.0 | 93.0 | 3.8 | 3.6 | — | 80.0 | 86.0 |
| 6 | 25V₂O₅—75TiO₂ | 31 | 250 | 0.4 | 40 | 70 | 0.75 | 80.0 | 93.0 | 3.0 | 4.0 | — | 74.4 | 85.0 |
| 7 | 30V₂O₅—70TiO₂ | 32 | 250 | 0.4 | 40 | 70 | 0.75 | 78.0 | 92.0 | 3.5 | 4.5 | — | 71.8 | 84.0 |
| 8 | 50V₂O₅—50TiO₂ | 17 | 250 | 0.4 | 40 | 70 | 0.87 | 72.2 | 84.9 | 9.8 | 5.3 | — | 61.3 | 83.0 |
| 9 | 75V₂O₅—25TiO₂ | 10 | 250 | 0.4 | 40 | 70 | 0.61 | 40.9 | 82.9 | 11.0 | 6.1 | — | 33.9 | 82.0 |
| 10 | 20V₂O₅—80TiO₂ | 29 | 270 | 0.4 | 40 | 70 | 1.07 | 91.5 | 92.5 | 3.5 | 4.0 | — | 84.6 | 86.0 |
| 11 | 20V₂O₅—80TiO₂ | 29 | 290 | 0.4 | 40 | 70 | 0.61 | 89.2 | 86.5 | 7.0 | 6.5 | tr. | 77.2 | 83.0 |
| 12 | 20V₂O₅—80TiO₂ | 29 | 250 | 0.4 | 40 | 70 | 1.50 | 91.0 | 93.7 | 2.5 | 3.8 | — | 85.0 | 86.0 |
| 13 | 20V₂O₅—80TiO₂ | 29 | 250 | 0.4 | 26 | 70 | 1.50 | 89.5 | 92.7 | 4.3 | 3.0 | — | 83.0 | 86.0 |
| 14 | 20V₂O₅—80TiO₂ | 29 | 250 | 0.4 | 15 | 70 | 1.50 | 84.0 | 93.2 | 3.8 | 3.0 | — | 78.0 | 86.0 |
| 15 | 20V₂O₅—80TiO₂ | 29 | 250 | 0.4 | 40 | 32 | 1.50 | 88.2 | 92.5 | 4.3 | 3.2 | — | 81.6 | 86.0 |
| 16 | 20V₂O₅—80TiO₂ | 29 | 250 | 0.4 | 40 | 10 | 1.50 | 85.0 | 93.1 | 3.9 | 3.0 | — | 79.0 | 86.0 |
| 17 | 20V₂O₅—79.4TiO₂—0.6Na₂O | 29 | 250 | 0.4 | 40 | 70 | 0.75 | 89.0 | 92.8 | 3.2 | 3.8 | — | 82.6 | 86.0 |
| 18 | 20V₂O₅—79.4TiO₂0.6SnO₂— | 29 | 250 | 0.4 | 40 | 70 | 0.75 | 89.5 | 93.0 | 3.0 | 3.7 | — | 83.2 | 86.0 |

τ - contact time, X - degree of conversion, S - selectivity, Y - yield of nicotinic acid, IDM - ideal displacement mode

We claim:

1. A process for preparing nicotinic acid from β-picoline comprising:
    a) oxidizing β-picoline with oxygen at a temperature of 250°–290° C. in the presence of aqueous vapor and a catalyst, said catalyst comprising oxides of vanadium and titanium and said catalyst having a specific surface area of 10–120 m²/g and
    b) isolating the nicotinic acid.

2. The process according to claim 1 wherein the mole ratio of oxides of titanium to oxides of vanadium is 4:1 to 19:1.

3. The process according to claim 1 wherein the process is carried out at mole ratios of O₂:β-picoline of 15:1 to 40:1 and H₂O:β-picoline of 10:1 to 70:1.

4. The process according to claim 1 wherein the catalyst further comprises additives.

5. The process according to claim 1 wherein the oxidation of β-picoline is a single-step gas-phase heterogeneous catalytic oxidation.

6. The process according to claim 1 wherein the nicotinic acid is isolated by crystallization at a temperature of 160°–200° C.

7. The process according to claim 1 wherein oxidization of β-picoline occurs in the presence of aqueous vapor, oxygen and nitrogen.

* * * * *